United States Patent [19]
Jazayeri

[11] Patent Number: 5,843,130
[45] Date of Patent: Dec. 1, 1998

[54] SYSTEM FOR DELIVERING ATRIAL DEFIBRILLATION SHOCKS

[75] Inventor: Mohammad R. Jazayeri, Brookfield, Wis.

[73] Assignee: Masood Akhtar, Elm Grove, Wis.

[21] Appl. No.: 829,162

[22] Filed: Mar. 31, 1997

[51] Int. Cl.[6] .................................................. A61N 1/39
[52] U.S. Cl. ...................................................... 607/5
[58] Field of Search ....................................... 607/4, 5, 14

[56] References Cited

U.S. PATENT DOCUMENTS

| | | | |
|---|---|---|---|
| 4,809,697 | 3/1989 | Causey, III et al. | 128/419 |
| 5,107,850 | 4/1992 | Olive | 128/705 |
| 5,207,219 | 5/1993 | Adams et al. | 128/419 |
| 5,269,298 | 12/1993 | Adams et al. | 607/5 |
| 5,282,836 | 2/1994 | Kreyenhagen et al. | 607/4 |
| 5,282,837 | 2/1994 | Adams et al. | 607/5 |
| 5,314,430 | 5/1994 | Bardy | 607/5 |
| 5,348,021 | 9/1994 | Adams et al. | 128/708 |
| 5,350,402 | 9/1994 | Infinger et al. | 607/5 |
| 5,350,404 | 9/1994 | Adams et al. | 607/5 |
| 5,366,486 | 11/1994 | Zipes et al. | 607/5 |
| 5,411,524 | 5/1995 | Rahul | 607/4 |
| 5,441,519 | 8/1995 | Sears | 607/5 |
| 5,464,433 | 11/1995 | White et al. | 607/5 |
| 5,470,342 | 11/1995 | Mann et al. | 607/5 |
| 5,486,198 | 1/1996 | Ayers et al. | 607/5 |
| 5,509,925 | 4/1996 | Adams et al. | 607/5 |
| 5,522,850 | 6/1996 | Yomtov et al. | 607/5 |
| 5,522,852 | 6/1996 | White et al. | 607/5 |
| 5,531,768 | 7/1996 | Alferness | 607/6 |
| 5,545,182 | 8/1996 | Stotts et al. | 607/5 |
| 5,549,641 | 8/1996 | Ayers et al. | 607/4 |
| 5,554,175 | 9/1996 | Alferness | 607/5 |
| 5,562,708 | 10/1996 | Combs et al. | 607/4 |
| 5,562,709 | 10/1996 | White | 607/5 |
| 5,578,062 | 11/1996 | Alt et al. | 607/5 |
| 5,601,609 | 2/1997 | Duncan | 607/5 |

OTHER PUBLICATIONS

Keelan et al., *Circulation* (suppl.) I–71: Abstract No. 0405, 69th Scientific Sessions (Nov. 1996).

Keelan et al., NASPE Abstracts, Pacing & Cardiac Electrophys. (PACE) 19: 647 (Abstract No. 324) (Apr. 1996).

*Primary Examiner*—Jeffrey R. Jastrzab
*Attorney, Agent, or Firm*—Godfrey & Kahn, S.C.

[57] ABSTRACT

A system for use in conjunction with an implantable automatic atrial defibrillation system is provided for delivering a defibrillation shock to the atria of a patient without inducing ventricular fibrillation, and a method of using the system. The system provides delivery of an atrial defibrillation shock synchronized only to beats during heart rate deceleration. With the present system, an atrial defibrillation shock is delivered after the passage of a minimum safe shock interval that is based upon a preset, predetermined minimum R—R deceleration interval length within a range of about 30–250 milliseconds.

10 Claims, 7 Drawing Sheets

SYSTEM FOR DELIVERING ATRIAL DEFIBRILLATION SHOCKS

BACKGROUND OF THE INVENTION

Atrial fibrillation is an abnormal irregular heart rhythm characterized by rapid, chaotic electrical activities in the upper chambers (atria) of the heart (e.g., a rate of 350 beats per minute or faster). The normal resting adult heart beats regularly at an average rate of 60 times per minute. The heart rate is governed by the speed of electrical signals originating from the sino-atrial (SA) node, the natural pacemaker of the heart, which is located within the wall of the right atrium. The signals from the SA node cause orderly contractions of the atrial chambers followed by contractions of the ventricles of the heart. Contractions of the atria deliver blood to the ventricles while contractions of the ventricles pump blood to the rest of the body, generating heart beats. During rest, the speed of the electrical signals originating from the SA node decreases resulting in a slowing of the heart rate. During exercise or excitement, the speed of signals from the SA node increases which accelerates the heart rate.

In atrial fibrillation, electrical signals are generated at different sites in the atria rather than by a single source, the SA node. These chaotic electrical waves lead to ineffective quivering of the atria rather than effective contractions that normally deliver blood to the ventricles. Atrial fibrillation also causes irregular and often rapid ventricular contractions, resulting in an irregular and rapid heart beat. Loss of normal atrial contractions along with the fast and irregular heart beatings impairs the ability of the heart to efficiently pump blood through the body. The symptoms of atrial fibrillation include palpitations, weakness, dizziness, shortness of breath, and even chest pains.

Atrial fibrillation may occur as a short-lasting or paroxysmal arrhythmia, for example, during the course of a viral infection of the heart, a heart attack, or following heart surgery. More often, atrial fibrillation is a chronic arrhythmia associated with diseased and enlarged atria. Approximately 1 in 10,000 otherwise healthy individuals have atrial fibrillation without any apparent cause. This condition, commonly known as "lone AF," is usually intermittent although it can become chronic in 25% of those affected.

The symptoms associated with atrial fibrillation can be very troublesome even in patients with otherwise normal or near-normal cardiac function. In some cases, this is due to a problem with the heart rate. In patients with diminished pumping function caused by preexisting heart diseases, the loss of atrial contraction may result in lowered exercise tolerance and even congestive heart failure. The most serious and potentially devastating complication in patients with atrial fibrillation is blood clot formation in the cardiac chambers.

In addition, the heart rate can be too high or too low. The electrical impulse must travel from the atria to the ventricles through the atrioventricular (AV) node. Owing to the frequent but irregular arrival of atrial electrical signals at the AV node, the majority of atrial signals are blocked within the AV nodal tissue and do not reach the ventricles, thereby protecting the ventricles from developing extremely rapid rates. Even so, the ventricles are driven to beat much more rapidly than normal. This rapid rate can make the patient feel poorly and cause shortness of breath, chest pains or a loss of consciousness.

The quivering atrial chambers in atrial fibrillation can also lead to sluggish blood flow. Stagnant blood tends to form blood clots along the walls of the atria. An embolism can occur if these blood clots dislodge and pass through the ventricles into the brain, lungs and other parts of the body. When a blood clot embolizes to the brain, a sudden onset of paralysis or embolic stroke results. Embolization to other vital organs such as the kidneys, lungs, and liver, will damage the respective organs. When clots reach the extremities, a sudden loss of blood circulation leads to the onset of cold arms, feet or legs.

The current treatment of atrial fibrillation involves controlling the risk factors, administering medications to slow the heart rate and/or convert the heart to normal rhythm, and preventing complications of blood clotting. Conventional treatment for a patient suffering from atrial fibrillation with rapid heart rate include: (1) medication to slow conduction through the AV node so that the ventricles beat at a more normal rate, (2) conversion of the atrial fibrillation to a normal rhythm with medications, electrical countershock or surgery, and, in extreme cases, (3) deliberate ablation of the AV node with radio frequency energy followed immediately with implantation of a permanent pacemaker.

Maintaining normal sinus rhythm after atrial fibrillation has stopped is not a simple matter. Most patients take antiarrhythmic drugs for maintaining normal sinus rhythm or preventing atrial fibrillation. The statistics show that patients who do not take any antiarrhythmic medication have about a 75% chance of returning to atrial fibrillation in one year. If they take older, more traditional antiarrhythmic drugs such as quinidine or procainamide, the chances are about 50%. Evidence also indicates that patients taking such older antiarrhythmic agents, especially those patients with heart muscle failure, may die earlier because of the risk of these medications causing other life-threatening heart rhythm disturbances or proarrhythmia. Therefore, these medications are typically initiated in the hospital while the patient is being monitored. Taking more recently developed antiarrhythmic drugs such as sotalol or amiodarone can reduce the chances of returning to atrial fibrillation to about 25%. However, although the risk of sudden death occurring from taking these drugs may be lower compared to older drugs, no antiarrhythmic medication is completely safe.

Patients with atrial fibrillation also have an increased risk for thromboembolic phenomenon. Administration of warfarin (coumadin), a blood thinning agent, reduces that risk. However, patients taking coumadin require close monitoring because of an increased risk of bleeding when the blood becomes too thin. Therefore, the benefit of using coumadin to prevent strokes may not outweigh the drawback of bleeding risks in elderly individuals or those who are prone to traumas that can result in serious bleeding.

Recent advancements in the management of atrial fibrillation include the development of ablative procedures and atrial defibrillators. One surgical procedure that has been proposed as a curative measure for prevention of atrial fibrillation and maintenance of sinus rhythm, is lengthy and associated with morbidity and mortality. Another procedure to prevent atrial fibrillation and maintain sinus rhythm using a transcatheter technique is in the early stages of investigation.

Implantable atrial defibrillators for detection and conversion of atrial fibrillation are generally known in the art, for example, as described in U.S. Pat. No. 5,486,198 (Ayers; InControl, Inc.), U.S. Pat. No. 5,562,708 (Combs; Medtronic, Inc.), and U.S. Pat. No. 5,411,524 (Rahul Mehra, Medtronic, Inc.). Implantable atrial defibrillators from such companies as Medtronic, Inc. (Minneapolis, Minn.), InControl, Inc. (Redmond, Wash.), and Cardiac Pacemakers, Inc. (St. Paul, Minn.) are currently undergoing clinical trials prior to full market release.

Generally, an atrial defibrillator is composed of a implantable housing and associated endocardial and intravascular lead(s) that are inserted and implanted into the ventricle and atria of the heart to provide sensing of the atrial activity and to deliver a defibrillating electrical shock. The housing can contain a mechanism for sensing and detecting activations of the ventricle and atria of the heart, a microprocessor, a ventricular pacing circuitry, a charger and a storage capacitor, a discharge circuit for discharging an electrical output from the storage capacitor through the intravascular lead to the atria, a battery to power the electrical components, and a mechanism to receive and transmit signals to and from an external source to set and reset parameters of the microprocessor. The sensing mechanism is coupled in data communication with the microprocessor which is programmed to perform various timing and data retention, manipulation and comparison functions, and to control the discharge of an atrial defibrillation (AD) shock via the intravascular lead(s).

One system presently under clinical investigation delivers atrial defibrillation shocks of much lower energy than those used for external defibrillation. However, the shocks that are delivered by that system are still painful to the patient. In addition, these shocks can induce ventricular arrhythmias when delivered during the vulnerable phase of the cardiac cycle.

The conventional approach to prevent ventricular arrhythmia induction by AD shocks is to synchronize the AD shock for delivery at the time of ventricular activation, or R wave. In that way, the shock is delivered outside of the T wave or "vulnerable period" of the cardiac cycle which should ordinarily be completed when ventricular activation occurs.

Atrial defibrillation (AD) shocks that are synchronized to normally conducted heart beats, that is, beats that originate in the sinus node and are conducted through the AV node and the His-Purkinje system, have been shown to be safe regardless of the previous R—R cycle length. However, in the presence of rapid heart rates, atrial defibrillation shocks can cause ventricular arrhythmias when synchronized to beats that are abnormally conducted because of bundle branch block or to beats originating from the ventricle.

Arrhythmia induction occurs when the atrial defibrillation shock is synchronized to a ventricular activation, known electrocardiographically as the "R wave," that is superimposed on or too closely spaced to the "T wave", e.g., repolarization or recovery phase of the previous cardiac cycle or beat. This is usually the case where the patient has abnormal ventricular conduction patterns in which there is a prolonged repolarization phase (e.g., T wave), which is frequent in patients with atrial fibrillation who have serious underlying structural heart disease.

In the implantable atrial defibrillation system described in U.S. Pat. No. 5,486,198 (Ayers), atrial defibrillation (AD) shocks are synchronized to beats (e.g., R wave) having a preceding cycle length that is longer than a predetermined value in order to avoid synchronizing an AD shock to a beat that falls within the vulnerable period (T wave phase) of the previous beat. The atrial defibrillator detects ventricular activations of the heart, measures the time intervals between immediately successive activations, and delivers a shock to the atria if certain parameters are met with respect to those time intervals.

Under Ayers system, atrial defibrillation shocks can be administered if the first measured time interval is longer than the second measured time interval. However, it has been found that ventricular fibrillation can occur under such conditions. Therefore, this system does not provide a protocol for delivery of an atrial defibrillation shock that is safe in all instances. This is particularly true for patients who have abnormal conduction patterns. Another drawback of the Ayers system is that the system requires long R—R intervals for synchronization that may not always be possible in some patients.

Therefore, an object of the invention is to develop an atrial defibrillation system that avoids delivery of an AD shock during the vulnerable period of the previous beat. Another object is to provide a system for delivery of an atrial defibrillation shock that is simple and does not require numerous measurements and comparisons.

SUMMARY OF THE INVENTION

These and other objects are achieved by the present invention which is a system for delivering an atrial defibrillation (AD) shock to the atria of a patient, and a method of using the system.

The present system can be used in conjunction with an implantable atrial defibrillator to control the timing of delivery of an AD shock to the heart of the patient. The system provides for delivery of atrial defibrillation shocks that are synchronized only to beats during heart rate deceleration, e.g., beats which R—R cycle or interval length is longer that the immediately preceding R—R interval length. It has been found according to the invention that an atrial defibrillation shock can be safely delivered following a minimum safe shock interval calculated based on a first measured R—R interval plus a predetermined deceleration interval value that is at least about 30 mseconds up to about 250 mseconds, preferably in a range of about 70–100 mseconds.

In one embodiment of the invention, the system operates in combination with processing elements of an atrial defibrillator to process signals of ventricular and atrial activations of the heart and to determine R—R interval lengths between three immediately successive ventricular activations (R waves), and deliver an AD shock that is synchronized to the third ($R_3$) wave, e.g., delivered substantially concurrently with the $R_3$ wave. In that application, the system is operable to determine the first interval (a). The system operates to determine a minimum safe shock interval for delivering an atrial defibrillation (AD) shock, and cause a defibrillation shock to be delivered to the atria if and when the time interval from the onset of the second beat ($R_2$ wave) is greater than or equal to the minimum safe shock interval. The minimum safe shock interval is calculated by adding the first $R_1$–$R_2$ interval and the predetermined minimum deceleration interval.

In another embodiment, the system is operable in conjunction with processing elements of the atrial defibrillator to deliver an AD shock that is not synchronized to an $R_3$ wave. In that application, the system is operable to measure a first $R_1$–$R_2$ interval between two successive ventricular activations, calculate a minimum safe shock interval equal to the first $R_1$–$R_2$ interval plus a predetermined minimum deceleration interval. Thus, an AD shock can be delivered if and when the atrial defibrillator does not detect any $R_3$ within the calculated interval.

In yet another embodiment of the invention, the system is operable to deliver an AD shock to the patient that is synchronized to a paced beat initiated by the defibrillator. With that system, a first $R_1$ wave and a second $R_2$ wave are detected, and a minimum safe shock interval is calculated based on the length of the $R_1$–$R_2$ interval plus a preselected minimum deceleration interval. The system determines whether the interval starting from the onset of the $R_2$ wave is greater than or equal to the minimum safe shock interval and, if so, causes a ventricular pacing impulse to be delivered to the ventricle and, after a time interval and before the vulnerable period of the paced beat, an electrical shock can be discharged in the atria.

The present system of employing a minimum R—R deceleration interval within a range of about 30–250 msec. to determine whether or not an atrial defibrillation (AD) shock can be safely administered following a ventricular activation (R wave), advantageously avoids the vulnerable period of the previous beat in all cases, regardless of the conduction pattern of the patient, and prevents the occurrence of ventricular fibrillation in such applications. The present invention, by enhancing the safety and feasibility of implantable defibrillation, will significantly improve the quality of life of patients with atrial fibrillation who are suitable candidates for such a therapy.

BRIEF DESCRIPTION OF THE DRAWINGS

Throughout the following views, reference numerals will be used in the drawings, and like reference numerals will be used throughout the several views and in the description to indicate corresponding parts of the invention.

DETAILED DESCRIPTION OF THE INVENTION

The present system controls delivery of AD shocks by an atrial defibrillator by synchronizing the AD shocks only to beats during heart rate deceleration and not to a beat that may fall within the vulnerable period (T wave phase) of the previous beat. The system advantageously prevents the occurrence of ventricular fibrillation in all patients, regardless of their conduction pattern.

Figure 1:
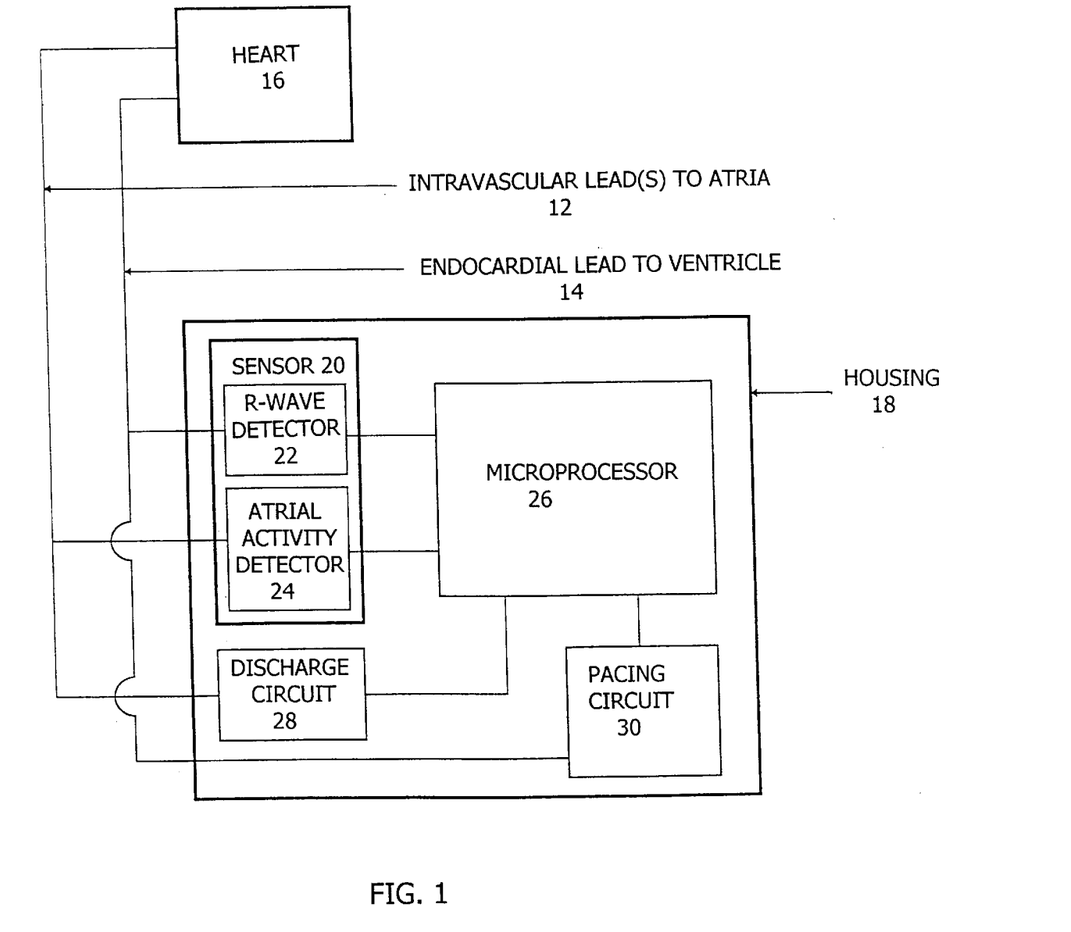
FIG. 1 is a block diagram depicting an implantable atrial defibrillator based on the prior art in conjunction with a heart, having a sensor, microprocessor, discharge circuit and intravascular/endocardial leads.

The present system for delivering an atrial defibrillation shock is accomplished using a microprocessor-based system for timing, processing, and control functions, and can be incorporated into a wide variety of implantable atrial defibrillators, as known and used in the art. Depicted in the block diagram of FIG. 1 are the main components of an atrial defibrillator, designated generally with the numeral 10. As shown, an atrial defibrillator 10 will include an intravascular lead 12 and endocardial lead 14 implantable into the atria and ventricle of a heart 16, and a housing 18 containing a sensor 20 composed of an R-wave detector 22 and an atrial activity detector 24, a microprocessor 26 and a discharge circuit 28. The system also contains a pacing circuit 30 capable of pacing the heart 16.

The microprocessor 20 includes processing elements as known and used in the art that are operable to time R—R intervals, retain data in memory, manipulate, calculate and compare data, and control discharge of an AD shock (not shown). Such processing elements are programmed to incorporate the present system to control delivery of AD shocks.

The system uses a minimum R—R interval deceleration value (Δ) to determine the minimum safe shock interval for safe delivery of an AD shock. The minimum R—R interval deceleration value (Δ) is the time in milliseconds that an $R_2$-shock interval must exceed a first measured and immediately preceding $R_1$–$R_2$ interval in order to provide a deceleration interval having a sufficient length to ensure that an AD shock can be safely delivered to a patient without inducing ventricular fibrillation.

According to the invention, use of a minimum R—R interval deceleration value (Δ) that falls within a range of about 30–250 mseconds will provide a reliable method for delivery of an AD shock regardless of the conduction pattern of the patient. The microprocessor is programmed with a specific minimum R—R interval deceleration value (Δ) within that range according to the clinical judgment of the attending physician or other health care professional based on clinical indicators of the patient. For example, the microprocessor is preferably programmed with an R—R interval deceleration value (Δ) in the range of about 30–100 msec. for normally conducted heart beats originating in the atrium. For supraventricular beats conducted with bundle branch block, the Δ value is preferably in the range of about 50–150 msec. To safely deliver an AD shock following heart beats with a ventricular origin, the Δ value is preferably within a range of about 50–250 msec. The specific Δ value is determined based on factors such as the site of origin and conduction pattern of the previous beat, the effect of medications, and varying conduction and repolarization properties among individuals.

The preset, predetermined minimum R—R interval deceleration value (Δ) is used to calculate the "minimum safe shock interval (c)" or time interval from the onset of a beat during heart rate deceleration that an atrial defibrillation (AD) shock can be safely administered to a patient without inducing ventricular fibrillation. The safe shock interval is calculated by adding the first $R_1$–$R_2$ interval length (a) and the predetermined minimum deceleration interval (Δ) over the range of about 30–250 msec.

In the use of the present system, an atrial defibrillator with a microprocessor incorporating the system is implanted under the skin of the patient with the leads implanted into the heart and positioned to optimize sensing, pacing and defibrillation energy requirements. The microprocessor is then programmed from an external source with a specific predetermined minimum R—R interval deceleration value ($\Delta$) or series of values depending upon the conduction patterns of the patent within the 30–250 msec. range as determined by the attending physician.

According to one embodiment of the invention, the system programmed into the microprocessor is operable to deliver an AD shock that is synchronized to the third ($R_3$) of three successive ventricular activations (R waves). With the system, the microprocessor is programmed to detect three immediately successive ventricular activations ($R_1$, $R_2$, $R_3$), to determine the first $R_1$–$R_2$ interval length (a), to calculate a minimum safe shock interval (c), to determine a second interval length (b) timed from the onset of the $R_2$ wave, and to cause an AD shock synchronized to the third $R_3$ wave to be delivered if interval (b) is equal to or greater than the minimum safe shock interval (c). Under those conditions, it is assured that the AD shock is synchronized to a beat of a "deceleration" interval (where b>a), and not an acceleration interval (where a>b) so that the AD shock is delivered outside of the vulnerable period (T wave) of the previous beat ($R_2$).

Figure 2:
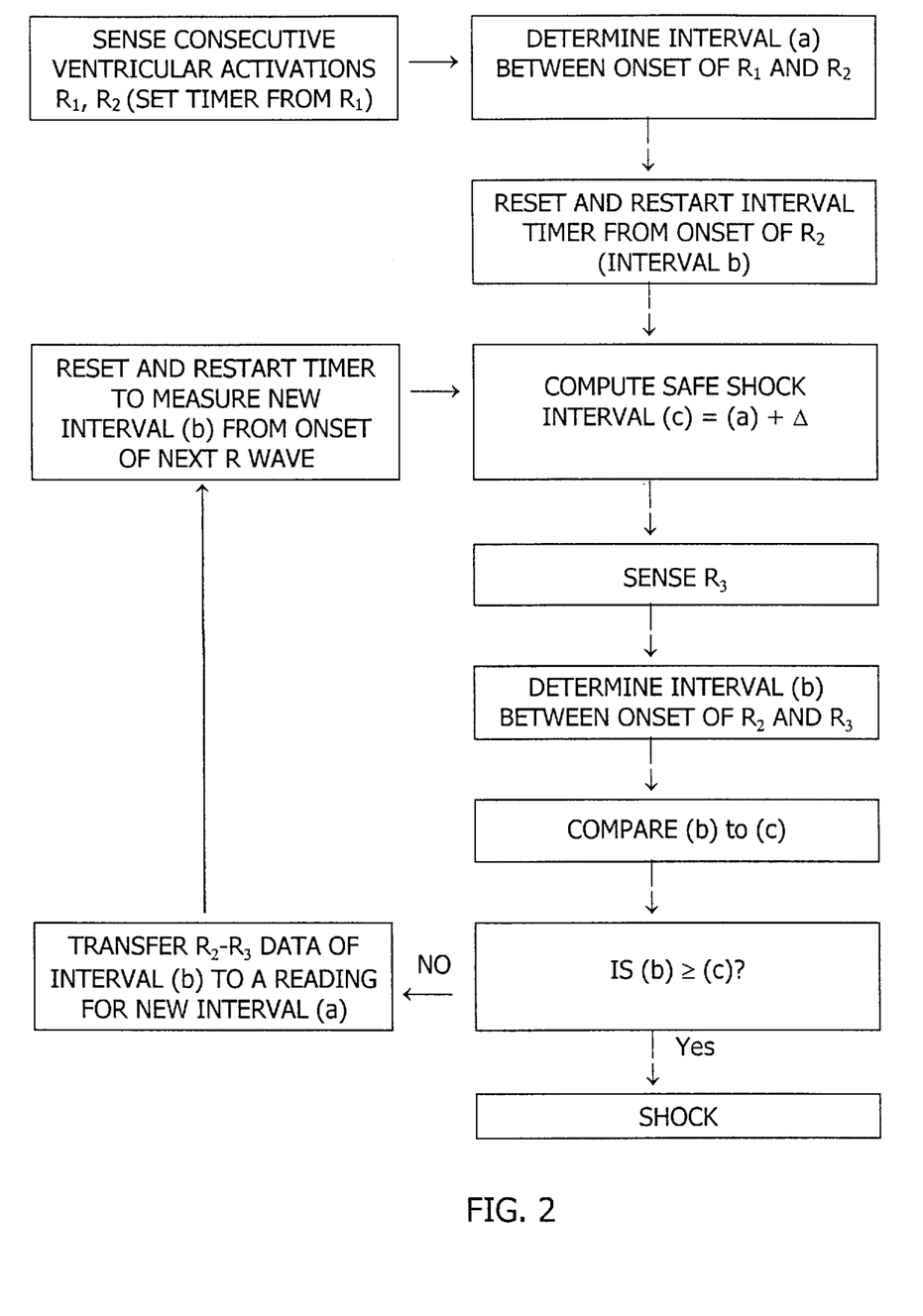
FIG. 2 is a flow diagram illustrating the implementation of an embodiment of the atrial defibrillation system of the invention for delivering synchronized shocks.
Figure 3:
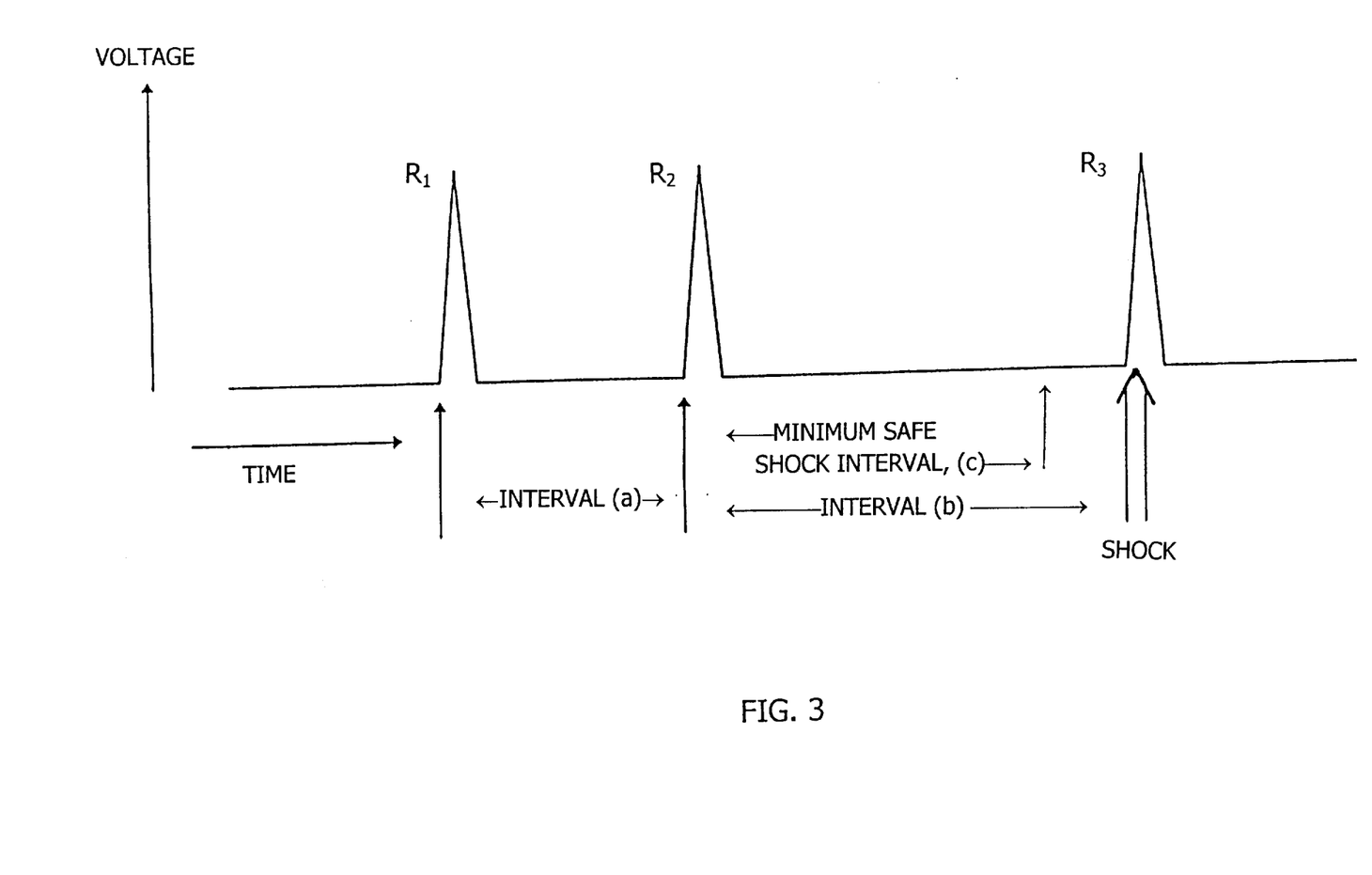
FIG. 3 is a graphical simulation of a surface electrogram illustrating the system of FIG. 2. $R_1$, $R_2$, and $R_3$ represent first, second and third ventricular activations or R waves. Intervals (a) and (b) represent the time interval between the onset of successive R waves, shown by the vertical arrows (↑). Interval (c) represents the calculated minimum safe shock interval and the application of an atrial defibrillation shock synchronized with the onset of $R_3$ wave, shown by the vertical arrow (⇑).

The operation of that system in an atrial defibrillator is shown in a flow diagram in FIG. 2 and the surface electrogram depicted in FIG. 3. When the sensing mechanism 20 of the atrial defibrillator 10 detects atrial fibrillation activity via an intravascular lead 12, the sensing mechanism 20 initiates detection of ventricular activations or R waves via an endocardial lead 14 which detects and sends signals of consecutive ventricular activations (R waves) to the microprocessor 26. At the onset of the first $R_1$ wave, the microprocessor 26 sets an interval timer element. When a second $R_2$ wave is detected, the microprocessor records the time in milliseconds at the onset of the $R_2$ wave, stores the time interval between waves $R_1$ and $R_2$ (interval "a") into an internal memory, and resets and restarts the timer to measure the time interval (b) from the onset of $R_2$.

The microprocessor 26 determines the minimum safe shock interval (c) for delivery of an atrial defibrillation shock that is synchronized to the $R_3$ wave by adding together the first $R_1$–$R_2$ interval length (a) and the preset, predetermined minimum deceleration value ($\Delta$) that has been programmed into the microprocessor. When the microprocessor senses an $R_3$ wave, the microprocessor computes interval (b) and then compares interval (b) to interval (c) and if interval (b) is equal to or greater than the minimum safe shock interval (c), the microprocessor causes an electrical shock that is synchronized to the $R_3$ wave to discharge to the atria.

If interval (b) is not equal to or greater than the minimum safe shock interval (c), the microprocessor will transfer the data of interval (b) ($R_2$ to $R_3$ interval) to a reading for a new interval (a), reset the timer to measure the time interval from the onset of $R_3$ as new interval (b), proceed to recalculate the minimum safe shock interval (c) based on the new interval (a) plus $\Delta$, and deliver an AD shock if new interval (b) is equal to or greater than new interval (c). These steps are repeated until a time interval (b) greater than or equal to minimum shock interval (c) is detected and the AD shock is delivered.

In another embodiment of the invention, the system is operable to deliver an unsynchronized atrial defibrillation (AD) shock, e.g., an AD shock that is delivered after a calculated minimum safe shock interval following a beat. In that system, the microprocessor of the atrial defibrillator is programmed to detect two immediately successive ventricular activations ($R_1$, $R_2$), to determine the $R_1$–$R_2$ interval length (interval "a"), to calculate a minimum safe shock interval ("c") for delivery of an AD shock after the second $R_2$ wave, to measure the interval ("b") following the second $R_2$ wave, and to cause an AD shock to be delivered if interval (b) is equal to or greater than the safe shock interval (c).

Figure 4:
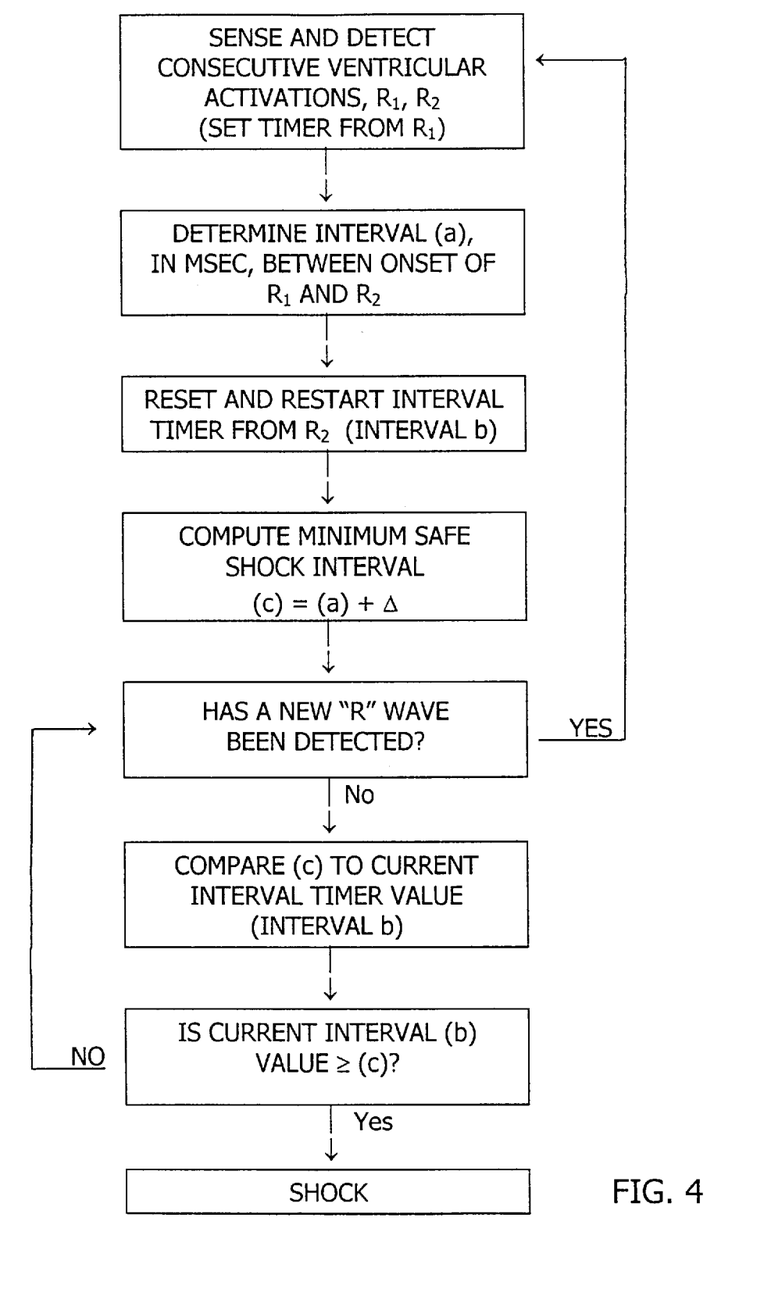
FIG. 4 is a flow diagram illustrating the implementation of a second embodiment of the system of the invention for delivering unsynchronized shocks.
Figure 5:
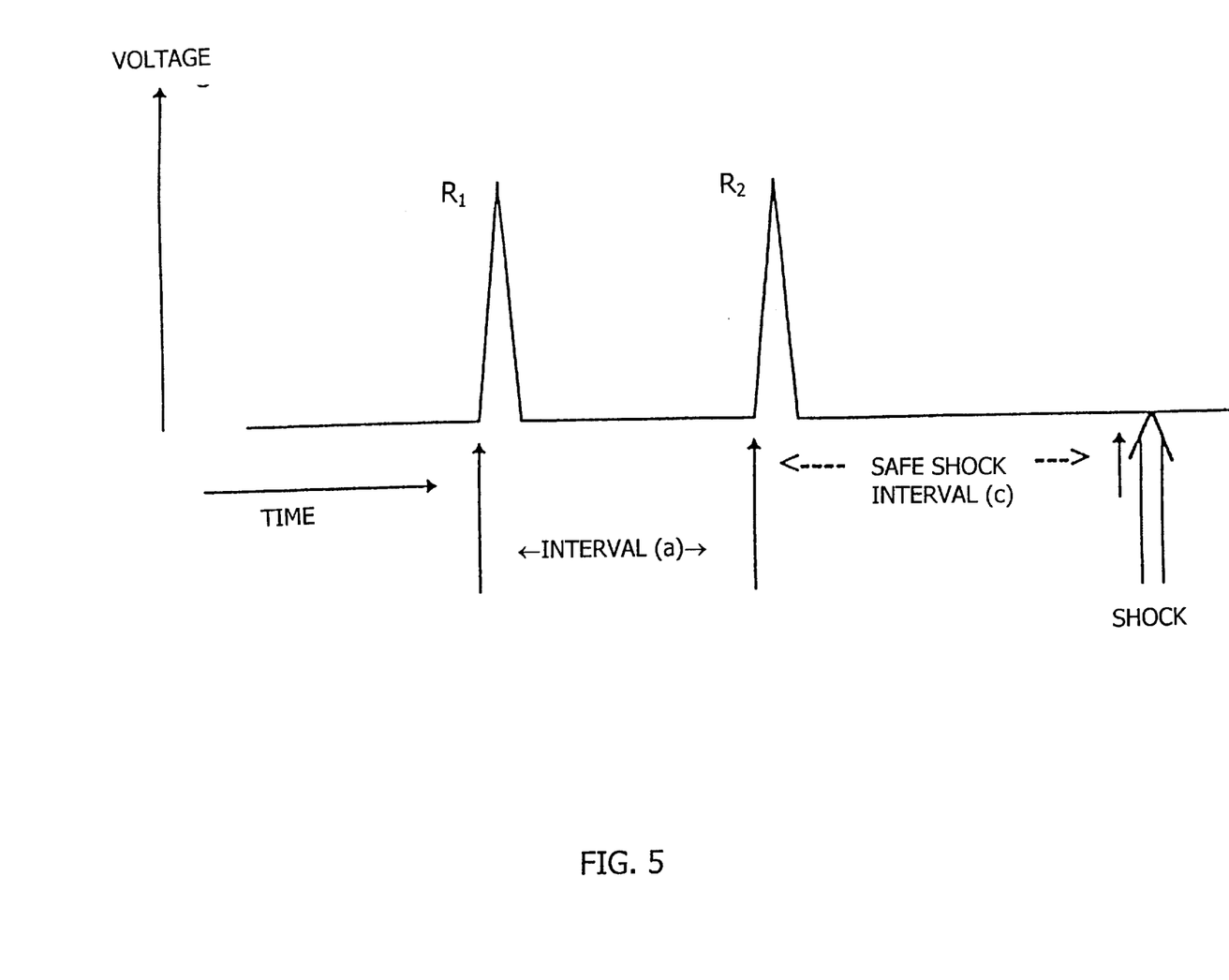
FIG. 5 is a graphical simulation of a surface electrogram illustrating the system of FIG. 4. The designations are the same as with FIG. 3, with interval (c) representing the calculated minimum safe shock interval, and the application of an atrial defibrillation shock shown by the arrow (⇑).
Figure 6:
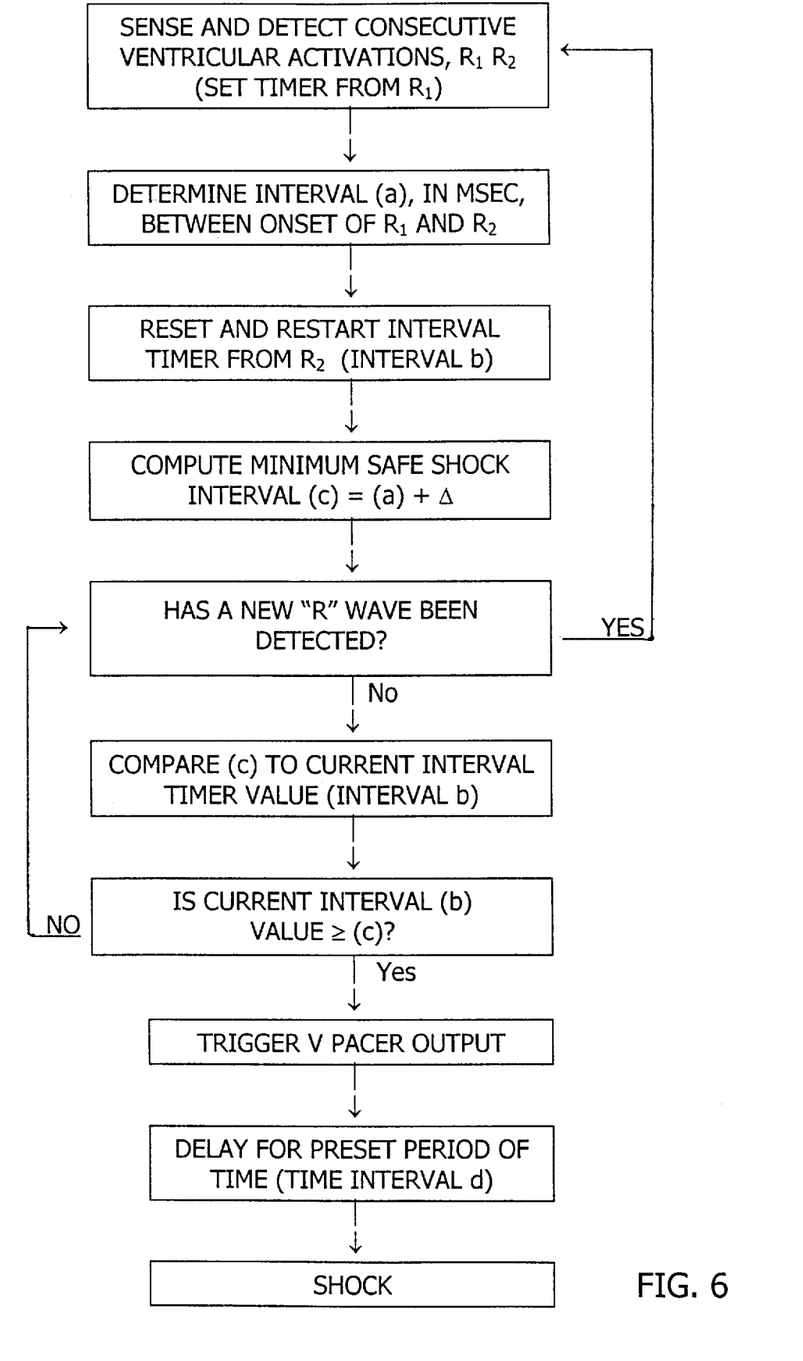
FIG. 6 is a flow diagram illustrating the implementation of a third embodiment of the system of the invention for delivering a paced beat synchronized shock.
Figure 7:
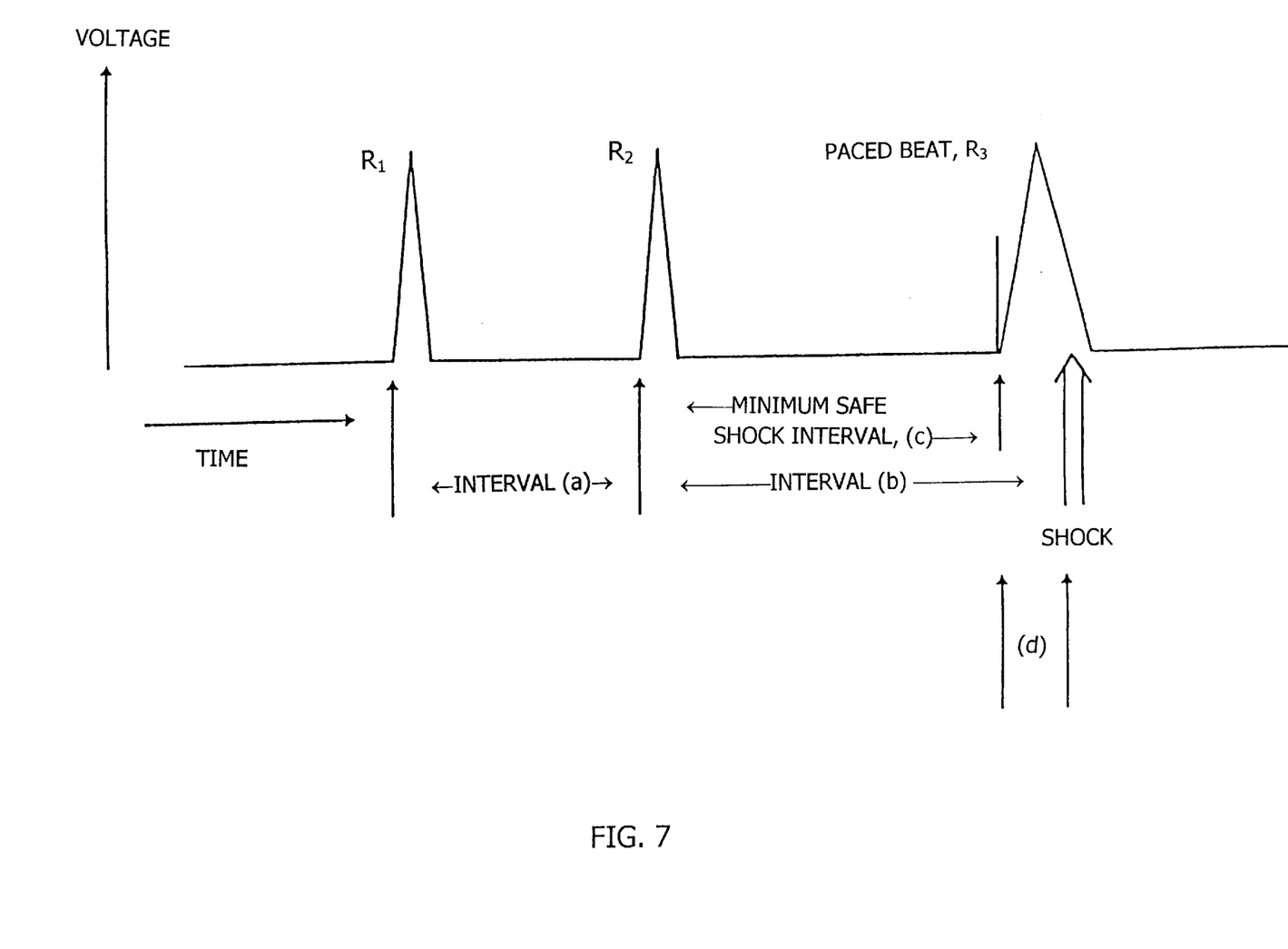
FIG. 7 is a graphical simulation of a surface electrogram illustrating the system of FIG. 6, with the designations being the same as in FIG. 5.

Such a system for delivering an unsynchronized atrial defibrillation (AD) shock is illustrated in a flow diagram in FIG. 4 and the surface electrogram in FIG. 5. When the sensing mechanism 20 initiates detection of atrial fibrillation activity via intravascular lead(s) 12, the sensing mechanism 20 initiates detection of ventricular activations or R waves via endocardial lead(s) 14, and sends signals of ventricular activation (R waves) to the microprocessor 26. At the onset of the first wave ($R_1$), the microprocessor 26 sets the interval timer. When a second R wave ($R_2$) is detected, the microprocessor records the time in milliseconds at the onset of the $R_2$ wave and stores the time interval between waves $R_1$ and $R_2$ (interval "a") into the internal memory, and resets and restarts the internal timer. The microprocessor computes the minimum safe shock interval ("c") by adding interval (a) to the preset, predetermined minimum deceleration interval ($\Delta$), and stores the value into memory. If no new R wave is detected, when the timer measuring the current interval (b) reaches a value that is equal to or greater than the minimum safe shock interval (c), the microprocessor 26 causes an electrical shock to discharge from a discharge circuit 28 into the intravascular lead(s) 12 to the atria of the heart 16.

In yet another embodiment, the system is used to deliver an atrial defibrillation (AD) shock that is synchronized to a paced beat initiated, for example, by the defibrillator, an implanted pacemaker, or an external source. With that system, the microprocessor 26 is programmed to detect two immediately successive ventricular activations ($R_1$, $R_2$), to determine the $R_1$–$R_2$ interval (interval "a"); to calculate a minimum safe shock interval ("c") for delivery of an AD shock after the second $R_2$ wave, to measure the interval ("b") following the second $R_2$ wave; if no new R wave is detected; to cause a ventricular pacing impulse to be delivered to the ventricle if interval (b) is equal to or greater than the minimum safe shock interval (c); to determine a time interval ("d") for delivery of an AD shock; and to cause an electrical shock to be delivered to the atria at the interval (d).

This system for delivering an atrial shock is illustrated in a flow diagram in FIG. 5. When the sensing mechanism 20 initiates detection of atrial fibrillation activity via intravascular lead(s) 12, the sensing mechanism 20 initiates detection of ventricular activations or R waves via the endocardial lead(s) 14, and sends signals of ventricular activation (R waves) to the microprocessor 26. At the onset of the first wave ($R_1$), the microprocessor sets an interval timer. When a second $R_2$ wave is detected, the microprocessor records the time in milliseconds at the onset of the $R_2$ wave and stores the time interval between waves $R_1$ and $R_2$ (interval "a") into an internal memory, and resets and restarts the interval timer to measure the time interval (b) from the onset of $R_2$. The microprocessor computes the minimum safe shock interval ("c") by adding interval (a) to the preset, predetermined minimum interval ($\Delta$) programmed into the microprocessor, and stores the (c) value into memory. If no new R wave is detected, when the value of the current interval ("b") being timed is greater than or equal to the minimum safe shock interval (c), the microprocessor 26 then causes a ventricular pacing impulse to be delivered into the ventricle, for example, by a pacing output circuit 30 via the intracardiac lead(s) 12. After a specified time interval ("d") from the pacing impulse, the microprocessor causes an electrical shock to discharge from the discharge circuit 28 into the intravascular lead(s) to the atria. The AD shock is discharged before the vulnerable period of the paced beat, preferably within about 1–100 msec. of the pacing impulse. The time interval (d) between the pacing impulse and the discharge of the AD shock is determined by the attending physician or health care professional based on clinical factors of the patient such as ventricular activation time, site of the pacing lead, the presence of medication, and the like.

The invention has been described by reference to detailed examples and methodologies. These examples are not meant to limit the scope of the invention. It should be understood that variations and modifications may be made while remaining within the spirit and scope of the invention, and the invention is not to be construed as limited to the specific embodiments shown in the drawings. The disclosures of the cited references are incorporated by reference herein.

What is claimed is:

1. A system for providing a defibrillation shock to the atria of the heart of a patient, comprising: one or more processing elements programmed to respond to a signal from a fibrillation detector and an R-wave detector, and:
   (a) to determine a first R—R interval between a first ventricular activation and an immediately successive second ventricular activation, and a second R—R interval between the second ventricular activation and an immediately successive third ventricular activation;
   (b) to determine a minimum safe shock interval by adding together the first R—R interval length and a predetermined minimum R—R deceleration value within a range of about 30–250 msec.; and
   (c) to cause the discharge of a defibrillation shock to the atria synchronized to the third ventricular activation when the second R—R interval length is greater than or equal to the minimum safe shock interval.

2. A system for providing a defibrillation shock to the atria of the heart of a patient; comprising one or more processing elements programmed to respond to a signal from a fibrillation detector and an R-wave detector, and:
   (a) to determine an R—R interval between a first ventricular activation and an immediately successive second ventricular activation;
   (b) to determine a minimum safe shock interval by adding together the R—R interval length and a predetermined minimum R—R deceleration value within a range of about 30–250 msec; and
   (c) to cause the discharge of a defibrillation shock to the atria after an interval beginning with the onset of the second ventricular activation and ending at or after a period of time equal in duration to the minimum safe shock interval.

3. A system for providing a defibrillation shock to the atria of the heart of a patient adapted to be used in conjunction with a defibrillator synchronized to a paced beat; comprising: one or more processing elements programmed to respond to a signal from a fibrillation detector and an R-wave detector, and:
   (a) to determine an R—R interval between a first ventricular activation and an immediately successive second ventricular activation;
   (b) to determine a minimum safe shock interval by adding together the R—R interval length and a predetermined minimum R—R deceleration value within a range of about 30–250 msec;
   (c) to cause the discharge of a ventricular pacing impulse to the ventricle after an interval beginning with the onset of the second ventricular activation and ending at or after a period of time equal in duration to the minimum safe shock interval;
   (d) to determine a time interval for discharge of an atrial defibrillation shock after the discharge of the ventricular pacing impulse and prior to the vulnerable period of the paced beat; and
   (e) to cause the discharge of a defibrillation shock to the atria after the time interval of step (d).

4. A method of delivering a defibrillation shock to the atria of the heart of a patient, comprising:
   a) implanting an atrial defibrillator comprising processing elements programmed with the system according to claim 1 into the patient;
   b) detecting atrial fibrillation activity;
   c) detecting successive ventricular activations;
   d) determining a first R-R interval measured from onset of a first ventricular activation and onset of a successive second ventricular activation, and a second R—R interval measured from the onset of the second ventricular activation and the onset of a successive third ventricular activation;
   e) determining a minimum safe shock interval by adding together the first R—R interval and a predetermined minimum R—R deceleration value in a range of about 30–250 msec.; and
   f) causing the defibrillation shock to be discharged to the atria when the second interval length is equal to or greater than the minimum safe shock interval;
   wherein the discharge of the defibrillation shock is synchronized to the third ventricular activation.

5. The method according to claim 4, further comprising prior to step b), programming the atrial defibrillation system with the minimum R—R deceleration interval value.

6. A method of delivering a defibrillation shock to the atria of the heart of a patient, comprising:
   a) implanting an atrial defibrillator comprising processing elements programmed with the system according to claim 2 into the patient;
   b) detecting atrial fibrillation activity;
   c) detecting successive ventricular activations;
   d) determining an R—R interval between a first ventricular activation and an immediately successive second ventricular activation;
   e) determining a minimum safe shock interval by adding together the R—R interval and a predetermined minimum R—R deceleration value within a range of about 30–250 msec; and
   f) causing the defibrillation shock to be discharged to the atria after an interval beginning with the onset of the second ventricular activation and ending at or after a period of time equal in duration to the minimum safe shock interval.

7. A method of delivering a defibrillation shock to the atria of the heart of a patient, comprising:
   a) implanting an atrial defibrillator comprising processing elements programmed with the system according to claim 3 into the patient;
   b) detecting atrial fibrillation activity;
   c) detecting successive ventricular activations;
   d) determining an R—R interval between a first ventricular activation and an immediately successive second ventricular activation;
   e) determining a minimum safe shock interval by adding together the R—R interval and a predetermined minimum R—R deceleration value within a range of about 30–250 msec;

f) causing a ventricular pacing impulse to be discharged to the ventricle after an interval beginning with the onset of the second ventricular activation and ending at or after a period of time equal in duration to the minimum safe shock interval;

g) determining a time interval for discharge of an atrial defibrillation shock after the ventricular pacing impulse and prior to the vulnerable period of the paced beat; and h) causing the defibrillation shock to be discharged to the atria after the time interval of step (g).

8. An implantable atrial defibrillator, comprising:

a sensor comprising an R-wave detector and an atrial fibrillation activity detector, the sensor connected to processing elements of the atrial defibrillator to send a signal of the R-waves to the processing elements;

the processing elements connected to a discharge circuit for discharging a defibrillation shock to the atria of the heart of a patient;

the processing elements responsive to signals from the sensor, and operable to time R—R intervals, retain data in memory, calculate data, compare data, and cause discharge of the defibrillation shock;

wherein the processing elements are programmed with the system of claim 1 to cause discharge of the defibrillation shock to the patient.

9. An implantable atrial defibrillator, comprising:

a sensor comprising an R-wave detector and an atrial fibrillation activity detector, the sensor connected to processing elements of the atrial defibrillator to send a signal of the R-waves to the processing elements;

the processing elements connected to a discharge circuit for discharging a defibrillation shock to the atria of the heart of a patient;

the processing elements responsive to signals from the sensor, and operable to time R—R intervals, retain data in memory, calculate data, compare data, and cause discharge of the defibrillation shock;

wherein the processing elements are programmed with the system of claim 2 to cause discharge of the defibrillation shock to the patient.

10. An implantable atrial defibrillator, comprising:

a sensor comprising an R-wave detector and an atrial fibrillation activity detector, the sensor connected to processing elements of the atrial defibrillator to send a signal of the R-waves to the processing elements;

the processing elements connected to a discharge circuit for discharging a defibrillation shock to the atria of the heart of a patient;

a pacing circuit connected to the processing elements to discharge a pacing impulse to the ventricle; and the processing elements responsive to signals from the sensor, and operable to time R—R intervals, retain data in memory, calculate data, compare data, cause a discharge of the ventricular pacing impulse, and cause a discharge of the defibrillation shock;

wherein the processing elements are programmed with the system of claim 3 to cause discharge of the defibrillation shock to the patient.

* * * * *